United States Patent
Desai et al.

(10) Patent No.: US 6,380,191 B1
(45) Date of Patent: Apr. 30, 2002

(54) ARYLTHIAZOLIDINEDIONE AND ARYLOXAZOLIDINEDIONE DERIVATIVES

(75) Inventors: Ranjit C. Desai, Franklin Park; Soumya P. Sahoo, Old Bridge; Jeffrey P. Bergman, Tenafly; Victoria K. Lombardo, Belle Meade; Edward J. Metzger, Edison; Hiroo Koyama, Hoboken, all of NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 09/595,840

(22) Filed: Jun. 16, 2000

Related U.S. Application Data

(60) Provisional application No. 60/139,929, filed on Jun. 18, 1999.

(51) Int. Cl.[7] .................. A61K 31/5377; C07D 236/06; C07D 413/10
(52) U.S. Cl. .................... 514/236.8; 514/376; 544/137; 548/227
(58) Field of Search .............................. 514/236.8, 376; 544/137; 548/227

(56) References Cited

U.S. PATENT DOCUMENTS

| | | |
|---|---|---|
| 4,200,642 A | 4/1980 | Schnur |
| 4,332,952 A | 6/1982 | Schnur |
| 4,342,771 A | 8/1982 | Schnur |
| 4,367,234 A | 1/1983 | Schnur |
| 4,423,233 A | 12/1983 | Schnur |
| 4,430,337 A | 2/1984 | Holland |
| 4,689,336 A | 8/1987 | Schnur |
| 4,695,634 A | 9/1987 | Schnur |
| 5,342,850 A | 8/1994 | Ohnota et al. |
| 5,391,565 A | 2/1995 | Hindley |
| 5,498,621 A | 3/1996 | Dow |
| 5,614,544 A | 3/1997 | Sohda et al. |
| 5,665,748 A | 9/1997 | Sohdo et al. |
| 5,801,173 A | 9/1998 | Lohray et al. |
| 5,932,601 A | 8/1999 | Sohdo et al. |
| 5,948,803 A | 9/1999 | Maeda |
| 6,008,237 A | 12/1999 | Sahoo |
| 6,166,043 A | * 12/2000 | Ikeda et al. .................. 514/342 |

FOREIGN PATENT DOCUMENTS

| | | |
|---|---|---|
| JP | 09012575 A | 1/1997 |
| WO | WO 91/05538 | 5/1991 |
| WO | WO 95/35108 | 12/1995 |
| WO | WO 97/27847 | 8/1997 |
| WO | WO 97/27857 | 8/1997 |
| WO | WO 97/28115 | 8/1997 |
| WO | WO 97/28137 | 8/1997 |
| WO | WO 97/28149 | 8/1997 |

OTHER PUBLICATIONS

Sohda, et al.., Chem. Pharm. Bull,. 30(10), pp. 3580–3600 (1982).
Sohda, et al.., Chem. Pharm. Bull., 30(10), pp. 3601–3616 (1982).
Schnur, et al. J. Med. Chem., 1986, vol. 29, pp. 770–778.
Dow, et al., J. Med. Chem,. 1991, vol. 34, pp. 1538–1544.
Cantello, et al., J. Med. Chem., 1994, vol. 37, pp. 3977–3985.
Willson, et al., J. Med. Chem., 1996, vol. 39, pp. 665–668.
Hulin, et al., Current Pharm. Design, 1996, vol.2, pp. 85–102.
Willson, et al., J. Med. Chem. 2000, vol. 43, pp. 527–550.

* cited by examiner

*Primary Examiner*—Robert W. Ramsuer
*Assistant Examiner*—Sonya N Wright
(74) *Attorney, Agent, or Firm*—James L. McGinnis; DAvid L. Rose

(57) ABSTRACT

Substituted 5-aryl-2,4-thiazolidinediones and oxazolidinediones are potent agonists of PPAR, and are therefore useful in the treatment, control or prevention of diabetes, hyperglycemia, hyperlipidemia (including hypercholesterolemia and hypertriglyceridemia), atherosclerosis, obesity, vascular restenosis, and other PPAR α and/or γ mediated diseases, disorders and conditions.

27 Claims, No Drawings

ARYLTHIAZOLIDINEDIONE AND ARYLOXAZOLIDINEDIONE DERIVATIVES

CROSS REFERENCE TO RELATED APPLICATIONS

This application claims priority from U.S. Provisional Application No. 60/139,929, filed on Jun. 18, 1999, which is incorporated by reference into this application in its entirety.

FIELD OF THE INVENTION

The instant invention is concerned with arylthiazolidinediones, aryloxazolinediones, and pharmaceutically acceptable salts thereof, which are useful as therapeutic compounds.

BACKGROUND OF THE INVENTION

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular diseases, including nephropathy, neuropathy, retinopathy, hypertension, stroke, and heart disease. Therefore, control of glucose homeostasis is a critically important approach for the treatment of diabetes.

There are two generally recognized forms of diabetes. In type I diabetes, or insulin-dependent diabetes mellitus (IDDM), patients produce little or no insulin, the hormone which regulates glucose utilization. In type II diabetes, or noninsulin dependent diabetes mellitus (NIDDM), patients often have plasma insulin levels that are the same or even elevated compared to nondiabetic humans; however, these patients have developed a resistance to the insulin stimulating effect on glucose and lipid metabolism in the main insulin-sensitive tissues, muscle, liver and adipose tissue and the plasma insulin levels are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in liver.

The common treatments for NIDDM, which have not changed substantially in many years, are all with limitations. While physical exercise and reductions in dietary intake of calories will dramatically improve the diabetic condition, compliance with this treatment is very poor because of well-entrenched sedentary lifestyles and excess food consumption, especially of high fat-containing food. Increasing the plasma level of insulin by administration of sulfonylureas (e.g. tolbutamide, glipizide) which stimulate the pancreatic β-cells to secrete more insulin or by injection of insulin after the response to sulfonylureas fails will result in high enough insulin concentrations to stimulate the very insulin-resistant tissues. However, dangerously low levels of plasma glucose can result from these last two treatments and increasing insulin resistance due to the even higher plasma insulin levels could occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in ameliorating many symptoms of NIDDM. These agents substantially increase insulin sensitivity in muscle, liver and adipose tissue in several animal models of NIDDM resulting in partial or complete correction of the elevated plasma levels of glucose without occurrence of hypoglycemia.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. See the *Merck Manual*, 16th Ed. 1992 (see for example pp. 1039–1040) and "Structure and Metabolism of Plasma Lipoproteins" in *Metabolic Basis of Inherited Disease*, 6th Ed. 1989, pp. 1129–1138.

One form of hyperlipidemia is hypercholesterolemia, characterized by the existence of elevated LDL cholesterol levels. The initial treatment for hypercholesterolemia is often to modify the diet to one low in fat and cholesterol, coupled with appropriate physical exercise, followed by drug therapy when LDL-lowering goals are not met by diet and exercise alone. LDL is commonly known as the "bad" cholesterol, while HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, but the quantities needed to achieve HDL raising are associated with undesirable effects, such as flushing.

Dyslipidemia is another term that is used to describe a combination of conditions that are associated with type II diabetes. Dyslipidemia refers generally to elevated LDL, elevated triglycerides and reduced HDL.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of hyperlipidemic drugs, herbicides and phthalate plasticizers. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). Identification of PPARα, a member of the nuclear hormone receptor superfamily activated by peroxisome proliferators, has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in LDL cholesterol, and they are used particularly for the treatment of hypertriglyceridemia.

The PPARγ receptor subtypes are involved in activating the program of adipocyte differentiation and are not involved in stimulating peroxisome proliferation in the liver. There are two isoforms of PPARγ: PPARγ1 and PPARγ2, which differ only in that PPARγ2 contains an additional 28 amino acids present at the amino terminus. The DNA sequences for the isotypes are described in Elbrecht, et al., BBRC 224; 431–437 (1996). In mice, PPARγ2 is expressed specifically in fat cells. Tontonoz et al., Cell 79: 1147–1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin J$_2$ derivatives have been identified as natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., *Molecular Endocrinology*, 6:1634–1641 (1992). It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARa and thyroid hormone receptor protein activity.

It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiatherosclerosis and antihyperlipidemic agents, and which may exert their effect through activation of PPARs.

It has been suggested that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85–102. Most of the glitazones that have been described in the literature are believed to bind almost exclusively to the PPARδ subtype.

All the glitazones that have progressed to clinical trials in human, and almost all of the glitazones that have been reported in the literature have the molecular motif of an aryl group attached to the 5-position of thiazolidinedione via a one carbon spacer. Although several compounds having a 4-(oxy)phenyl group directly attached to the 5-position of thiazolidinedione have been prepared and tested as potential antidiabetic agents, they have been stated to lack hypoglycemic activity.

Thus, the compound 5-[4-[2-(2-benzoxazolylmethylamino) ethoxy]phenyl]-2,4-thiazolidinedione (1) showed no antihyperglycemic activity in ob/ob mice, and subsequent studies showed this compound to require relatively high amounts for PPARδ activation. (Cantello et al, *J. Med. Chem.*, 1994, 37:3977–3985 and Willson et al, *J. Med. Chem.*, 1996, 39:665–668).

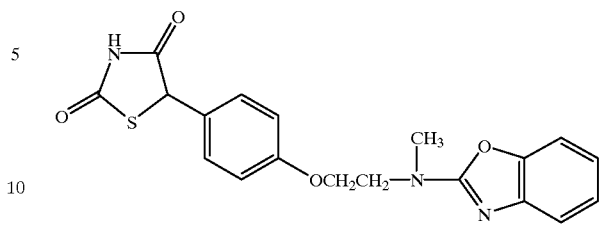

1

The compound 5-[4-(phenylethoxy)phenyl]-2,4-thiazolidinedione (2) showed no antihyperglycemic effect in diabetic mouse model, even though it may have aldose reductase inhibitory activity. (Sohda et al, *Chem. Pharm. Bull.*, 1982, 30:3580–3600, and Sohda et al, *Chem. Pharm. Bull.*, 1982, 30:3601–3616). Examples of other phenylthiazolidinedione aldose reductase inhibitors include 5-[4-(4-chlorophenoxy)phenyl]-2,4-thiazolidinedione, 5-[4-(4-chlorobenzyloxy)phenyl]-2,4-thiazolidinedione, 5-[4-(2-pyridylethoxy)phenyl]-2,4-thiazolidinedione, 5-[4-(6-methyl-2-pyridylethoxy)phenyl]-2,4-thiazolidinedione, and 5-[4-(2-thienylethoxy)phenyl]-2,4-thiazolidinedione. (Sohda et al, *Chem. Pharm. Bull.*, 1982, 30:3601–3616).

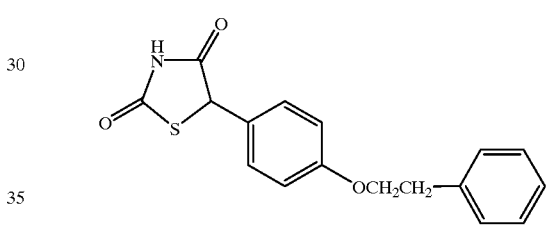

2

PCT Published Application WO97/22600 discloses antihyperglycemic 5-[3-(carboxamido)phenyl]-2,4-thiazolidinediones of the formula

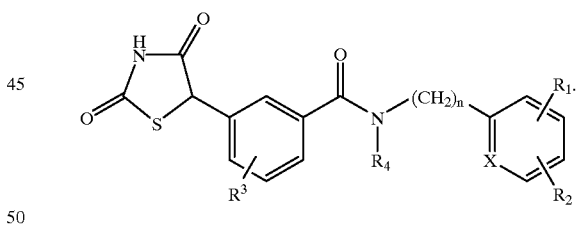

Some oxazolidinedione compounds having the oxazolidinedione ring bound directly to the aryl group have been synthesized and have been found to have some hypoglycemic activity. See for example (1) R. Dow, et al., J. Med. Chem., 34, 1538–1544 (1991); (2) R. Schnur, et al., J. Med. Chem. 29, 770–778 (1986); (3) U.S. Pat. No. 4,367,234; (4) U.S. Pat. No. 4,342,771; and (5) U.S. Pat. No. 4,332,952.

The present inventors have found that certain substituted 5-aryl-2,4-thiazolidinediones and 5-aryl-2,4-oxazolidinediones having at least one cycloalkyl or heterocyclic substituent on the ring $Ar^2$ of Formula I are potent agonists of PPAR, in particular the (α and/or δ subtypes, and especially the γ subtype or both the α/γ subtypes. These compounds are therefore useful in the treatment, control or prevention of diabetes, hyperglycemia, dyslipidemia, hyperlipidemia (including hypercholesterolemia and hypertriglyceridemia), atherosclerosis, obesity, vascular restenosis, and other PPAR α and/or γ mediated diseases, disorders and conditions.

SUMMARY OF THE INVENTION

The present invention provides compounds having the structure of Formula I:

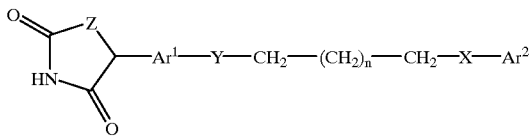

I wherein
Ar$^1$ is
  (1) arylene or
  (2) heteroarylene,
    wherein said arylene or heteroarylene is optionally substituted with from 1 to 4 groups independently selected from R$^a$, R, or a mixture thereof.
Ar$^2$ is
  (1) aryl or
  (2) heteroaryl,
    wherein said aryl or heteroaryl is substituted with 1–2 groups independently selected from R, provided that if only one cycloalkyl is present on Ar2, the cycloalkyl is not in the ortho position, and said aryl or heteroaryl is optionally further substituted with from 1–3 groups independently selected from R$^a$;
X and Y are independently O, S, N-R$^b$, or CH$_2$;
Z is O or S;
n is 0 to 3;
R is
  (1) C$_{3-8}$ cycloalkyl, optionally substituted with 1–15 halogen atoms, 1–3 groups independently selected from C$_{1-6}$ alkyl, and mixtures thereof; or
  (2) a 3–10 membered heterocycle containing one or more heteroatoms selected from N, S, O, and SO2, said heterocycle being optionally substituted with 1–3 halogen atoms or one to three C$_{1-6}$ alkyl groups;
R$^a$ is
  (1) C$_{1-15}$ alkanoyl,
  (2) C$_{1-15}$ alkyl,
  (3) C$_{2-15}$ alkenyl,
  (4) C$_{2-15}$ alkynyl,
  (5) halo,
  (6) OR$^b$,
  (7) aryl, or
  (8) heteroaryl,
    wherein said alkyl, alkenyl, alkynyl, and alkanoyl are optionally substituted with from 1–5 groups selected from R$^c$, and said aryl and heteroaryl are optionally substituted with 1 to 5 groups selected from R$^d$;
R$^b$ is
  (1) hydrogen,
  (2) C$_{1-10}$alkyl,
  (3) C$_{2-10}$alkenyl,
  (4) C$_{2-10}$alkynyl,
  (5) aryl,
  (6) heteroaryl,
  (7) aryl C$_{1-15}$ alkyl,
  (8) heteroaryl C$_{1-15}$ alkyl,
  (9) C$_{1-15}$ alkanoyl,
  (10) C$_{3-8}$ cycloalkyl,
    wherein said alkyl, alkenyl, and alkynyl are optionally substituted with one to four substituents independently selected from R$^c$, and said cycloalkyl, aryl and heteroaryl are optionally substituted with one to four substituents independently selected from R$^d$;
R$^c$ is
  (1) halo,
  (2) aryl,
  (3) heteroaryl,
  (4) CN,
  (5) NO$_2$,
  (6) OR$^f$,
  (7) S(O)$_m$R$^f$, m=0, 1 or 2, provided that R$^f$ is not H when m is 1 or 2;
  (8) NR$^f$R$^f$,
  (9) NR$^f$COR$^f$,
  (10) NR$^f$CO$_2$R$^f$,
  (11) NR$^f$CON(R$^f$)$_2$,
  (12) NR$^f$SO$_2$R$^f$, provided that R$^f$ is not H,
  (13) COR$^f$,
  (14) CO$_2$R$^f$,
  (15) CON(R$^f$)$_2$,
  (16) SO$_2$N(R$^f$)$_2$,
  (17) OCON(R$^f$)$_2$, or
  (18) C$_{3-8}$cycloalkyl,
    wherein said cycloalkyl, aryl and heteroaryl are optionally substituted with 1 to 3 groups of halo or C$_{1-6}$ alkyl;
R$^d$ is
  (1) a group selected from R$^c$,
  (2) C$_{1-10}$ alkyl,
  (3) C$_{2-10}$ alkenyl,
  (4) C$_{2-10}$ alkynyl,
  (5) aryl C$_{1-10}$ alkyl, or
  (6) heteroaryl C$_{1-10}$ alkyl,
    wherein said alkyl, alkenyl, alkynyl, aryl C$_{1-10}$ alkyl, and heteroaryl C$_{1-10}$ alkyl are optionally substituted with a group independently selected from R$^e$;
R$^e$ is
  (1) halogen,
  (2) amino,
  (3) carboxy,
  (4) C$_{1-4}$alkyl,
  (5) C$_{1-4}$alkoxy,
  (6) hydroxy,
  (7) aryl,
  (8) aryl C$_{1-4}$ alkyl, or
  (9) aryloxy;
R$^f$ is
  (1) hydrogen,
  (2) C$_{1-10}$ alkyl,
  (3) C$_{2-10}$ alkenyl,
  (4) C$_{2-10}$ alkynyl,
  (5) aryl,
  (6) heteroaryl,
  (7) aryl C$_{1-15}$ alkyl,
  (8) heteroaryl C$_{1-15}$ alkyl,
  (9) C$_{1-15}$ alkanoyl,
  (10) C$_{3-8}$ cycloalkyl;
    wherein said alkyl, alkenyl, alkynyl, aryl, heteroaryl, alkanoyl and cycloalkyl are optionally substituted with one to four groups independently selected from R$^e$;
or a pharmaceutically acceptable salt thereof.

DETAILED DESCRIPTION OF THE INVENTION

The invention has numerous preferred embodiments, including:

compounds of Formula I wherein Z is sulfur;

compounds of Formula I, wherein Z is O;

compounds of Formula I wherein $Ar^1$ is arylene optionally substituted with 1–4 groups independently selected from $R^a$, R, or a mixture thereof;

compounds of Formula I wherein $Ar^1$ is phenylene optionally substituted with 1–2 groups independently selected from halogen and $C_{1-4}$ alkyl;

compounds of Formula I wherein X and Y are independently $CH_2$, O or S;

compounds of Formula I in which n is 1 or 2; and compounds of Formula I wherein X and Y are each O or S.

The invention also comprises a subset of compounds having the structure of Formula I, wherein $Ar^2$ is aryl, wherein said aryl is substituted with one $R^a$ group in the position ortho to X and is further substituted with 1–2 groups independently selected from R and optionally 1–2 groups independently selected from Ra. In a preferred embodiment of this subset, $R^a$ that is in the position ortho to X is selected from the group consisting of:

(1) $C_{3-10}$ alkyl optionally substituted with 1–4 groups independently selected from halo and $C_{3-6}$ cycloalkyl, (2) $C_{3-10}$ alkenyl, or (3) $C_{3-8}$ cycloalkyl.

In a preferred embodiment of the above subset of compounds, $Ar^2$ is a phenyl ring.

In one embodiment of the last subset of compounds, two of the optional substituents $R^a$ are on adjacent carbon atoms on the Ar2 phenyl ring and are joined to form a 5- or 6-membered aromatic heterocyclic ring fused to $Ar^2$, said ring containing 1–2 heteroatoms independently selected from N, O, and S(O)m, where m is 0–2, said heterocyclic ring and $Ar^2$ together being substituted with 1–2 groups independently selected from R, one $R^a$ group in the position ortho to X, and optionally 1–2 additional groups independently selected from $R^a$. In preferred examples of this last embodiment, the aromatic heterocyclic ring fused to $Ar^2$ is selected from isoxazole, thiophene, thiophene S-oxide, thiophene S-dioxide, and furan.

A preferred embodiment comprises compounds of Formula I having the structure shown as Formula Ia:

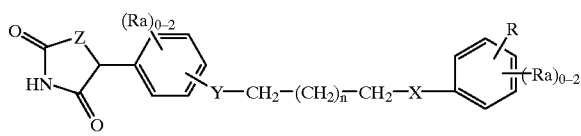

Ia wherein X, Y, Z, n, R, and $R^a$ are as previously defined. More specific embodiments of the compounds having Formula Ib include:

compounds of Formula Ia where Z is S;

compounds of Formula Ia where Z is O;

compounds of Formula Ia where Y is S or O, and X is O;

compounds of Formula Ia where one Ra group is ortho to X and is $C_{3-4}$ alkyl;

compounds of Formula Ia where n is 1 or 2; and compounds of Formula Ia where
  Z is O or S;
  X is O;
  Y is
    (1) O or
    (2) S; and one group Ra is ortho to X and is $C_{3-4}$ alkyl.

A highly preferred embodiment of this last group of compounds includes compounds where Z is O and R is cyclohexyl.

Specific examples of compounds of this invention are provided herein in Examples 1–12 by name and by structural formula.

The invention further includes pharmaceutical compositions comprising any of the compounds described above and a pharmaceutically acceptable carrier.

The compounds as defined above are useful in the following methods of treating, controlling, and preventing diseases, as well as other diseases not listed below:

(1) a method for treating or controlling diabetes mellitus in a mammal which comprises administering to the mammal a therapeutically effective amount of a compound of Formula I;

(2) a method for treating, controlling or preventing hyperglycemia in a mammal which comprises administering to the mammal a therapeutically effective amount of a compound of Formula I;

(3) a method for treating, controlling or preventing hyperlipidemia in a mammal which comprises administering to the mammal a therapeutically effective amount of a compound of Formula I;

(4) a method for treating, controlling or preventing obesity in a mammal which comprises administering to the mammal a therapeutically effective amount of a compound of Formula I;

(5) a method for treating, controlling or preventing hypercholesterolemia in a mammal which comprises administering to the mammal a therapeutically effective amount of a compound of Formula I;

(6) a method for treating, controlling or preventing hypertriglyceridemia in a mammal which comprises administering to the mammal a therapeutically effective amount of a compound of Formula I; and (7) a method for treating, controlling or preventing dyslipidemia in a mammal which comprises administering to the mammal a therapeutically effective amount of a compound of Formula I.

Definitions

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each having from 3 to 10 carbon atoms. The term also includes a monocyclic ring fused to an aryl group in which the point of attachment is on the non-aromatic portion. Examples of cycloalkyl include cyclopropyl, cyclopentyl, cyclohexyl, cycloheptyl, and the like.

"Aryl" (and "arylene") means mono- or bicyclic aromatic rings containing only carbon ring atoms. The term also includes an aryl group fused to a monocyclic cycloalkyl or monocyclic heterocyclic group in which the point(s) of attachment is on the aromatic portion. "Heterocycle" and "heterocyclic" means a fully or partially saturated ring containing at least one heteroatom selected from N, S and O, each of said rings having from 3 to 10 atoms. Examples of aryl include phenyl, naphthyl, indanyl, indenyl, tetrahydronaphthyl, 2,3-dihydrobenzofuranyl, benzopyranyl, 1,4-benzodioxanyl, benzoxazolyl, benzisoxazolyl, and the like. Examples of heterocycles include tetrahydrofuran, piperazine, and morpholine.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b) pyridyl, quinolyl, indolyl, isoquinolyl, dibenzofuran and the like.

"Halogen" includes fluorine, chlorine, bromine and iodine.

The term "ortho-substituted" means the substituent is attached to a ring atom that is adjacent to the point of attachment to the backbone of the molecule. "Meta-substituted" and "para-substituted" are defined analogously based on the point of attachment of the ring to the backbone of the molecule.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

Compounds of the present invention are potent agonists of varioius peroxisome proliferator activator receptor subtypes, particularly PPARα and/or PPARγ. Compounds of the present invention may be selective agonists of one receptor subtype, e.g. PPARγ agonists, or they may be agonists of more than one receptor subtypes, e.g. dual PPARα/γ agonists. Compounds of the present invention are useful in treating, controlling or preventing diseases, disorders or conditions, wherein the treatment is mediated by the activation of an individual PPAR subtype (α or γ), or a combination of PPAR subtypes (e.g. α/γ). Thus one aspect of the present invention provides a method for the treatment, control or prevention of such diseases, disorders, or conditions in a mammal which comprises administering to such mammal a therapeutically effective amount of a compound of Formula I. The diseases, disorders or conditions for which compounds of the present invention are useful in treating, controlling or preventing include, but are not limited to, (1) diabetes mellitus, (2) hyperglycemia, (3) obesity, (4) hyperlipidemia, (5) hypertriglyceridemia, (6) hypercholesterolemia (including raising HDL levels), (7) atherosclerosis, (8) vascular restenosis, (9) irritable bowel syndrome, (10) pancreatitis, (11) abdominal obesity, (12) adipose cell tumors, (13) adipose cell carcinomas such as liposarcoma, (14) dyslipidemia, and (15) other disorders where insulin resistance is a component including Syndrome X and ovarian hyperandrogenism (polycystic ovarian syndrome). Also included are inflammatory diseases, such as inflammatory bowel disease, Crohn's disease, and ulcerative colitis.

Another aspect of the invention provides a method for the treatment, control, or prevention of hypercholesterolemia which comprises administering to a mammal in need of such treatment a therapeutically effective amount of an agonist of both PPARα and PPARγ (PPARα/γ dual agonist). The dual agonist may be advantageously administered with a cholesterol biosynthesis inhibitor, particularly an HMG-CoA reductase inhibitor such as lovastatin, simvastatin, pravastatin, fluvastatin, atorvastatin and rivastatin.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 (rosiglitazone), and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARδ agonists such as those disclosed in WO97/28149;

(g) antiobesity compounds such as fenfluramine, dexfenfluramine, phentiramine, sulbitramine, orlistat, neuropeptide Y5 inhibitors, and $\beta_3$ adrenergic receptor agonist;

(h) ileal bile acid transporter inhibitor.

BIOLOGICAL ASSAYS

A. White Adipose Tissue in vitro Assay

This assay measures the efficacy of the instant compounds to enhance the insulin activation of $^{14}$C-glucose incorporation into glycogen in white adipose tissue (WAT) in a 5 hour completely in vitro system. All procedures are performed in medium 199 containing 1% bovine serum albumen, 5 mM HEPES, and antibiotic (100 units/ml penicillin, 100 μg/ml streptomycin sulfate, 0.25 μg/ml amphotericin B), hereafter called culture medium. Epididimyl fat pads are minced with scissors into small fragments , approximately 1 mm in diameter. Minced WAT fragments (100 mg) are incubated in a total volume of 0.9 ml culture medium containing 1 mU/ml insulin and test compound in tissue culture incubator at 37° C. with 5% $CO_2$ with orbital shaking for 3 hours. $^{14}$C-labeled glucose is added and incubation continued for 2 hours. Tubes are centrifuged at low speed, infranatant is removed and 1 M NaOH is added. Incubation of alkali-treated WAT for 10 minutes at 60° C. solubilizes tissue. Resulting tissue hydrolysate is applied to Whatman filter paper strips which are then rinsed in 66% ethanol followed by 100% acetone which removes unincorporated $^{14}$C-glucose from bound $^{14}$C-glycogen. The dried paper is then incubated in solution of amyloglucosidase to cleave glycogen into glucose. Scintillation fluid is added and samples are counted for $^{14}$C activity. Test compounds that resulted in $^{14}$C activity substantially above incubations with insulin alone are considered active insulin-enhancing agents. Active compounds were titrated to determine the compound concentration which resulted in 50% of maximum enhancement of insulin activation and were termed $EC_{50}$ values.

B. Gal-4 hPPAR Transactivation Assays (a) Plasmids

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5x)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter.

(b) Cell culture and Transactivation Assays

COS-1 cells were seeded at $12 \times 10^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% $CO_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5x)-tk-luc reporter vector and 0.0002 μg of pCMV-lacZ as an internal control for transactivation efficiency. Cells were incubated in the transfection mixture for 5 h at 37° C. in an atmosphere of 10% $CO_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In Vivo Studies

Male db/db mice (10–11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3–5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

Methods of Synthesis

Compounds of formula I may be prepared according to the methods outlined in the schemes. The variables in the schemes, unless otherwise specified, have the same meanings as defined above under formula I. The intermediates and starting materials in Schemes 1–4 are written with respect to methylesters, but other esters (e.g. $C_1$–$C_{15}$ esters) can also be used, as well as trialkyl silane groups attached to the carboxyl. Similarly, other acids, bases, halogenating agents and solvents can be used for many of the reactions in Schemes 1–4, as will be readily determined by practitioners in the field.

Scheme 1

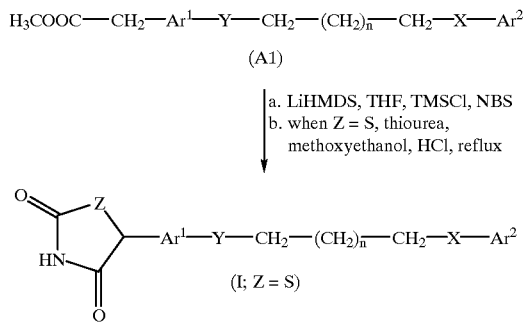

Alpha-bromination of an arylacetate ester intermediate A1 with a halogenating agent (e.g. N-bromosuccinimide) in the presence of a base produces a halo intermediate which may be ring-closed with thiourea (Z=S) in the presence of aqueous strong acid or sodium acetate in an alcoholic solvent such as 2-methoxyethanol at elevated temperatures to give the title aryl-thiazolidinones (I; Z=S).

Scheme 2

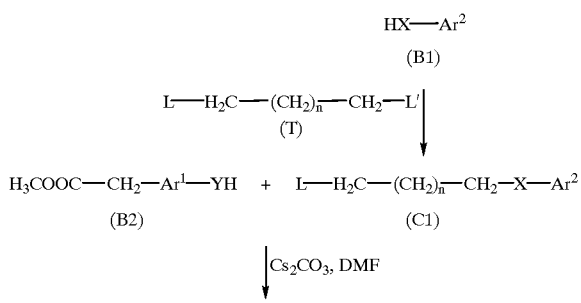

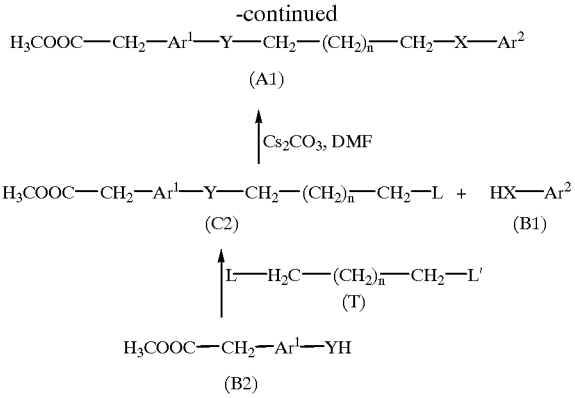

L and L' are same or different leaving groups

Scheme 2 shows the synthesis of intermediate A1, which contains an $Ar^1$ moiety and an $Ar^2$ moiety connected by a $\geq 4$ atom tether. Intermediate A1 may be prepared by convergent synthesis by first attaching the tether T having two terminal leaving groups to either $Ar^1$ or $Ar^2$; in T, L and L' represent independently of each other a conventional leaving group such as halide (preferably bromide) and sulfonyloxy (e.g. mesylate or tosylate). Treatment of the tethered molecule C1 or C2 with the other aryl moiety B2 or B1, respectively in the presence of an inorganic base (e.g. $Cs_2CO_3$) in DMF solution provides the tethered arylacetate ester intermediate A1. The starting material T, B1, and B2 are either commercially available or may be prepared using known organic synthesis procedures. Compounds of formula B2 may be prepared according to the methods described in published PCT Applications 97/27857, 97/28115 and 97/28137.

Scheme 3

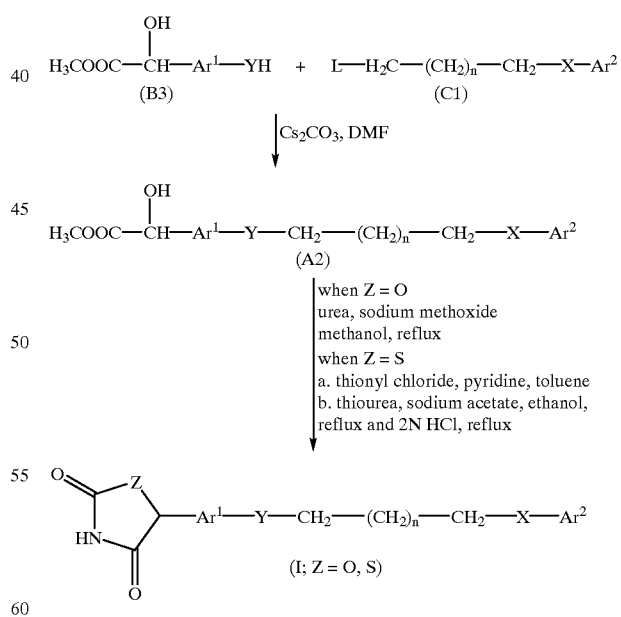

In Scheme 3 an appropriately substituted mandelic acid ester B3 is reacted with the $Ar^2$ derivative having a leaving group L, C1, in the presence of an inorganic base such as cesium carbonate. The resulting product A2 is cyclized with urea in the presence of a base such as sodium methoxide to form the desired product (I; Z=O). Alternatively, the hydroxy group of A2 may be converted to the corresponding chloride using thionyl chloride, and the resulting compound is ring-closed as described previously in Scheme 1 to provide compounds of formula I wherein Z=S. The starting materials for the synthesis depicted in Scheme 3 are either commercially available or may be prepared using known organic synthesis methodologies.

Scheme 4

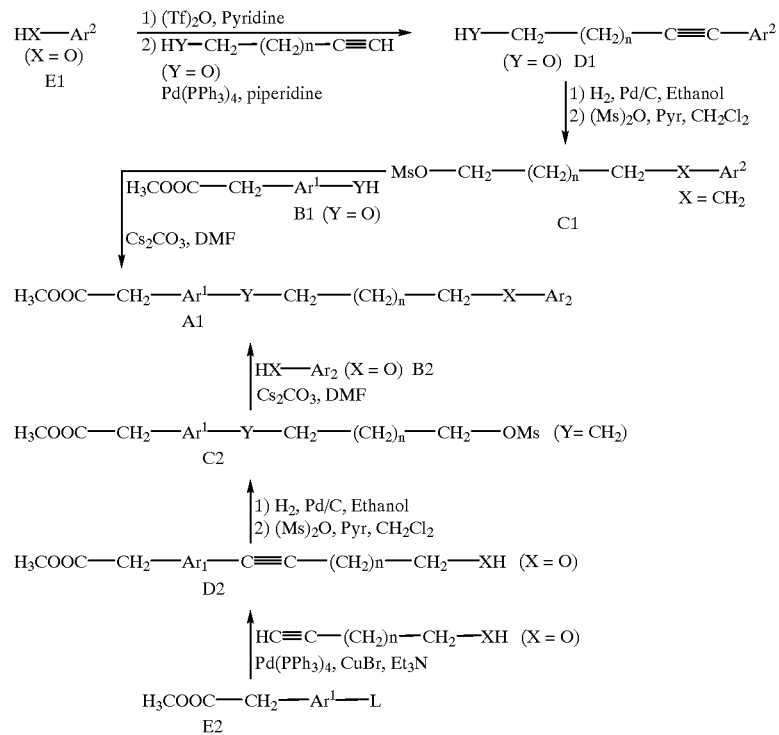

L is a leaving group
(Tf)$_2$O = Trifluoromethanesulfonic Anhydride, (Ms)$_2$O = Methanesulfonic Anhydride Scheme 4 shows the synthesis of intermediate A1, which contains an Ar$^1$ moiety and an Ar$^2$ moiety connected by a ≧4 atom tether in which one of X or Y is oxygen. Palladium catalyzed addition of an alkyne to either an arylbromide (E1) or triflate (E2) gives D1 or D2, respectively. Hydrogenation of the alkyne (D1 or D2) at atmospheric pressure afforded the fully saturated material, C1 or C2. which was coupled to either B1 or B2 in the presence of an inorganic base (e.g. Cs2CO3) in dimethylformamide solution to provide the tethered arylacetate ester intermediate A1. The starting materials for the synthesis depicted in scheme 4 are either commercially available or may be prepared using known organic synthesis methodologies.

EXAMPLES

The following Examples are provided only to illustrate the invention and are not to be construed as limiting the invention in any manner.

Example 1

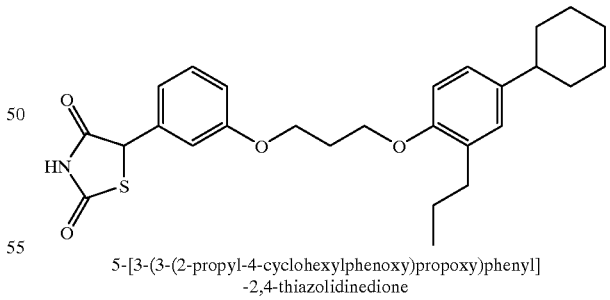

5-[3-(3-(2-propyl-4-cyclohexylphenoxy)propoxy)phenyl]
-2,4-thiazolidinedione

Step A: Preparation of 2-propyl-4-cyclohexyl phenol

A solution of 4-cyclohexylphenol (10 g), allyl bromide (13.74 g) and potassium carbonate (9.42 g) in acetone (150 mL) was kept at reflux for 10–12 h. The solution was cooled, filtered and concentrated under reduced pressure to provide 4-cyclohexyl allyloxyphenol (12.4 g). This product was used as such for Step C.

A solution of 4-cyclohexyl allyloxyphenol (12.3 g) in ortho-dichlorobenzene (50 mL) was kept at reflux for 36 h.

The mixture was cooled to room temperature and chromatographed over silica gel to afford 2-propenyl-4-cyclohexylphenol (11.0 g). This material was dissolved in methanol (150 mL) and hydrogenated over Pd/C (1.2 g) at 50 psi. The reaction was filtered through Celite and concentrated in vacuo to afford the title compound (11.0 g).

$^1$H NMR (400 MHz, CDCl$_3$): δ 6.96 (s, 1H); 6.93 (d, 1H, J=8 Hz); 6.7 (d, 1H, J=8 Hz); 4.51 (s, 1H); 2.57 (t, 2H, J=7.6 Hz); 2.42 (m, 1H); 1.86–1.2 (m, 12H); 0.99 (t, 3H, J=7.2 Hz).

Step B: Preparation of ethyl 3-(3-bromopropoxy) mandelate

A solution of ethyl 3-hydroxymandelate (10.0 g), 1,3-dibromopropane (41.16 g) and potassium carbonate (8.08 g) in dry DMF (150 mL) was stirred at 40° C. overnight. The reaction mixture was partitioned between ethyl acetate and 1.0 N HCl. The organic layer was washed twice with water, once with brine and then dried over sodium sulfate. The organic layer was then filtered and the solvent removed in vacuo. The resulting oil was chromatographed on silica gel, using a gradient of 100% hexane to methylene chloride-hexane to yield the titled compound.

$^1$H NMR (400 MHz, CDCl$_3$): δ 7.3 (d, 1H, J=8.0 Hz); 7.03 (d, 1H, J=7.6 Hz); 7.0 (s, 1H); 5.14 (d, 1H, J=5.5 Hz); 4.28–4.2 (m, 2H); 4.13 (t, 2H, J=5.9 Hz); 3.62 (t, 2H, J=6.5 Hz); 2.33 (quint, 2H, J=5.8 Hz); 1.26 (t, 3H, J=7.0 Hz).

Step C: Preparation of ethyl 3-(3-(2-propyl-4-cyclohexylphenoxy) propoxy)mandelate A solution of 2-propyl-4-cyclohexylphenol (0.9 g) (as prepared in Step A), potassium carbonate (0.69 g) and ethyl 3-(3-bromopropoxy)mandelate (1.18 g) in DMF (30 mL) was stirred at 40° C. for 30 h. The reaction mixture was partitioned between ethyl acetate and 1.0 N HCl. The organic layer was washed twice with water, once with brine and then dried over sodium sulfate. The organic layer was then filtered and the solvent remove in vacuo. The resulting oil was chromatographed on silica gel, using ethyl acetate/hexane to yield the titled compound.

$^1$H NMR (400 MHz, CDCl$_3$): δ 7.3–6.78 (m, 7H); 5.12 (d, 1H, J=5.0 Hz); 4.27 (q, 2H, J=7.2 Hz); 4.19 (t, 2H, J=6.0 Hz); 4.14 (t, 2H, J=6.0Hz); 3.42 (d, 1H, J=5.0 Hz); 2.57 (t, 2H, J=7.4 Hz); 2.43–2.2 (m, 3H); 1.85–1.36 (m, 12H); 1.25 (t, 3H, J=7.2 Hz); 0.94 (t, 3H, J=7.3 Hz).

Step D: Preparation of ethyl α-chloro-3-(3-(2-propyl-4-cyclohexylphenoxy) propoxy)phenylacetate Thionyl chloride (0.15 mL) was added to a solution of ethyl 4-(3-(2-propyl-4-cyclohexylphenoxy)propoxy) mandelate of Step C (0.71 g), pyridine (0.19 mL), and toluene (15 mL). The reaction mixture was stirred 6–7 h and then partitioned between ethyl acetate and water. The organic layer was washed twice with water, once with brine, dried over sodium sulfate, and filtered. The solvent was removed in vacuo and the resulting oil was used as such for the next step.

Step E: Preparation of 5-[3-(3-(2-propyl-4-cyclohexylphenoxy)propoxy) phenyl]-2,4-thiazolidinedione The residual oil was dissolved in ethanol (15 mL). Thiourea (0.14 g) and sodium acetate (0.14 g) were added. The mixture was heated to reflux for 6 h. Hydrochloric acid (5 mL, 6 N) was added, and the mixture was heated at 115° C. for 6 h. The mixture was partitioned between ethyl acetate and water. The organic layer was washed twice with water, dried over sodium sulfate, filtered and evaporated to an oil, which was chromatographed over silica gel with 3% acetonitrile in methylene chloride to afford the title compound.

$^1$H NMR (400 MHz, CDCl$_3$): δ 8.14 (brs, 1H), 7.35–6.8 (m, 7H); 7.02–6.79 (m, 8H); 5.32 (s, 1H); 4.2 (t, 2H, J=6.3 Hz); 4.14 (t, 2H, J=5.8 Hz); 2.57 (t, 2H, 7.6 Hz); 2.43 (m, 1H); 2.28 (quint, 2H, J=6.3 Hz); 1.85–1.25 (m, 12H); 0.94 (t, 3H, J=7.5 Hz). MS: m/e=466(M$^+$).

Example 2

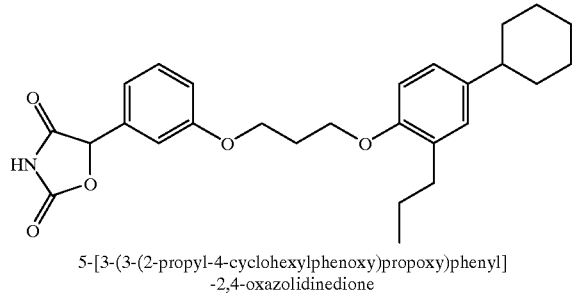

5-[3-(3-(2-propyl-4-cyclohexylphenoxy)propoxy)phenyl]-2,4-oxazolidinedione

Step A: Preparation of ethyl 3-(3-(2-propyl-4-cyclohexylphenoxy)propoxy)mandelate This compound was prepared according to the procedure described in EXAMPLE 1, STEPS A–C.

Step B: 5- [3-(3-(2-propyl-4-cyclohexylphenoxy)propoxy)phenyl]-2,4-oxazolidinedione The above compound (1.5 g) was dissolved in absolute ethanol (30 mL) and to this was added sodium ethoxide (1.3 M equivalent) and urea (0.28 g). The solution was stirred initially at room temperature and then at reflux for 15 h. After cooling, the solution was concentrated under reduced pressure and the residue was acidified using 6N HCl, extracted with ethyl acetate, washed with water and brine, and then concentrated. Purification of the residue using flash chromatography over silica-gel using acetonitrile-dichloromethane afforded the desired compound.

$^1$H NMR (400 MHz, CDCl$_3$): δ 7.70 (brs, 1H); 7.39–6.97 (m, 6H); 6.79 (d, 1H, J=8.6 Hz); 5.77 (s, 1H); 4.21 (t, 2H, J=6.2 Hz); 4.14 (t, 1H, J=5.8 Hz); 2.58 (t, 2H, J=7.4 Hz); 2.43 (m, 1H); 2.29 (quint, 2H, J=6.1 Hz); 1.85–1.23 (m, 12H); 0.94 (t, 3H, J=7.4 Hz). MS: m/e=452(M$^+$).

Example 3

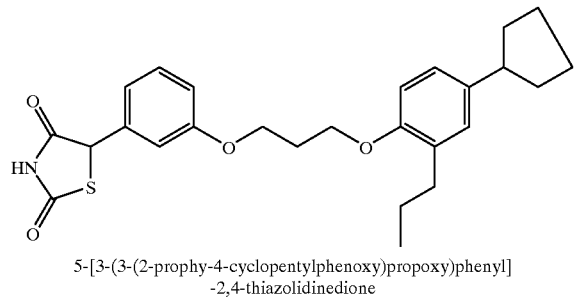

5-[3-(3-(2-prophy-4-cyclopentylphenoxy)propoxy)phenyl]-2,4-thiazolidinedione

Using 4-cyclopentylphenol, this compound was synthesized in a similar manner as described for the preparation of EXAMPLE 1 (STEPS A–E).

$^1$H NMR (300 MHz, CDCl$_3$): δ 8.09 (brs, 1H); 7.34–6.79 (m, 7H); 5.31 (s, 1H); 4.18 (t, 2H, J=6.1 Hz); 4.12 (t, 2H, J=5.9 Hz); 2.9 (m, 1H); 2.55 (t, 2H, J=7.4 Hz); 2.26 (quint, 2H, J=6.0 Hz); 2.05–1.49 (m, 10H); 0.92 (t, 3H, J=7.5 Hz). MS: m/e=454(M$^+$).

Example 4

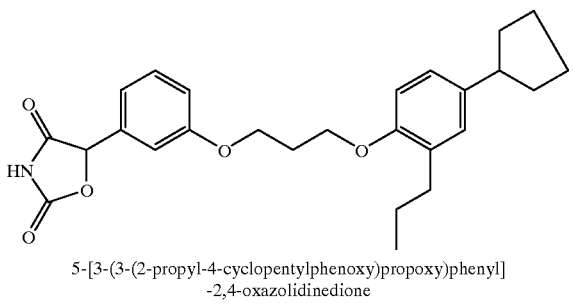

5-[3-(3-(2-propyl-4-cyclopentylphenoxy)propoxy)phenyl]-2,4-oxazolidinedione

Beginning with 4-cyclopentylphenol, this target was synthesized in an identical manner to that used for the preparation of EXAMPLE 2.

$^1$H NMR (300 MHz, CDCl$_3$): δ 7.95 (brs, 1H); 7.35 (d, 1H, J=7.6 Hz); 7.03–6.95 (m, 5H); 6.9 (d, 2H, J=8.5 Hz); 5.75 (s, 1H); 4.19 (t, 2H, J=6.2 Hz); 4.12 (t, 2H, J=5.9 Hz); 2.9 (m, 1H); 2.55 (t, 2H, J=7.6 Hz); 2.27 (quint, 2H, J=6.1 HZ); 2.1–1.4 (m, 10H); 0.92 (t, 3H, J=7.3 Hz). MS: m/e= 438(M$^+$)

Example 5

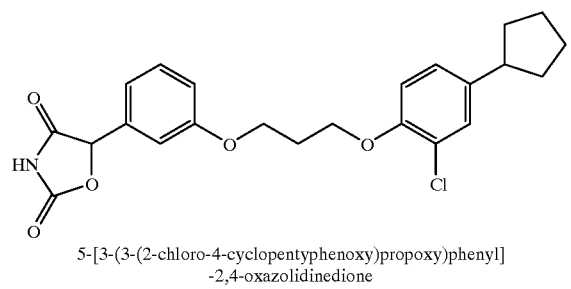

5-[3-(3-(2-chloro-4-cyclopentyphenoxy)propoxy)phenyl]-2,4-oxazolidinedione

Step A: Preparation of 2-chloro-4-cyclopentylphenol

A solution of 4-cyclopentylphenol (4 g) and diisobutylamine (0.35 mL) in toluene (75 mL) was heated to 70° C. with stirring. Sulfuryl chloride (2.0 mL) was introduced via syringe and the reaction stirred for 2 h at 70° C., then cooled to room temperature. The reaction mixture was concentrated in vacuo and the resulting oil subjected to chromatography on silica gel using hexane/ethyl acetate eluent to afford the title compound (3.5 g). $^1$H NMR (400 MHz, CDCl$_3$): δ 7.19 (d, 1H, J=2.0 Hz); 7.06 (dd, 1H, J=2.2 Hz, 6.2 Hz); 6.94 (d, 1H, J=8.6 Hz); 5.37 (s, 1H); 2.92 (quint, 1H, J=7.0 Hz); 2.03 (m, 2H); 1.80 (m, 2H); 1.67 (m, 2H); 1.53 (m, 2H). MS: m/e=197(M$^+$).

Step B: Preparation of 5-[3-(3-(2-chloro-4-cyclopentylphenoxy)propoxy)phenyl]-2,4-oxazolidinedione This compound was prepared according to the procedure described in Example 2, Steps A and B. $^1$H NMR (400 MHz, CDCl$_3$): δ 7.83 (brs, 1H); 7.28 (t, 1H, J=6.1 Hz); 7.24 (d, 1H, J=2.1 Hz); 7.08–6.99 (m, 3H); 6.88 (d, 1H, J=8.4 Hz); 5.78 (s, 1H); 4.21 (t, 2H, J=6.0 Hz); 4.18 (t, 2H, J=6.0 Hz); 2.92 (quint, 1H, J=7.0 Hz); 2.31 (quint, 2H, J=6.1 Hz); 2.03 (m, 2H); 1.80 (m, 2H); 1.67 (m, 2H); 1.53 (m, 2H). MS: m/e=430(M$^+$)

Example 6

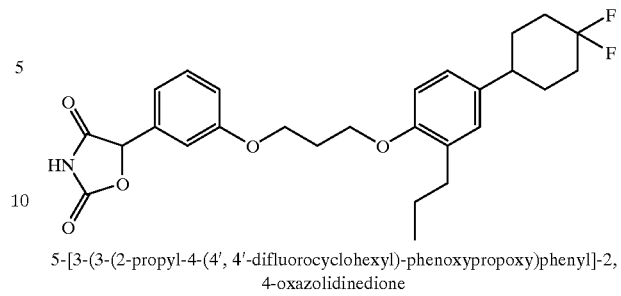

5-[3-(3-(2-propyl-4-(4',4'-difluorocyclohexyl)-phenoxypropoxy)phenyl]-2,4-oxazolidinedione Step A: Preparation of 2-propyl-4-(4',4,-difluorocyclohexyl)phenol Commercially available 4-(4-hydroxyphenyl)cyclohexanone was first converted to the corresponding 4-(2-propyl-4-hydroxyphenyl)cyclohexanone according to the procedure described in Example 1, Step A.

To a solution of 4-(2-propyl-4-hydroxyphenyl)cyclohexanone (2.32 g) in THF (30 mL) was added at 0° C. bis(2-methoxyethyl)amino sulfur trifluoride (5.5 mL) and the solution was stirred for 36 h. At the end, the reaction mixture was cooled to 0° C. and the excess of reagent was carefully destroyed using a saturated solution of NaHCO$_3$.

The reaction mixture was diluted with ethyl acetate (150 mL) and the organic phase was washed with water (3×50 mL), brine, dried over sodium sulfate and concentrated under reduced pressure and the resulting oil was chroamatographed on silica gel using a gradient of 100% hexane to ethyl acetate-hexane to yield the title compound.

$^1$H NMR (400 MHz, CDCl$_3$): δ 6.95 (m, 2H), 6.72 (d, 1H, J=8.2 Hz); 4.6 (brs, 1H); 2.6–1.6 (m, 13H); 0.99 (t, 3H, J=7.2 Hz).

Step B: Preparation of ethyl 3-(3-(2-propyl-4-(4',4'-difluorocyclohexyl)-phenoxypropoxy)mandelate This compound was prepared according to procedure described in Example 1, Steps B–C.

Step C: 5-[3-(3-(2-propyl-4-(4',4'-difluorocyclohexyl)-phenoxypropoxy)phenyl]-2,4-oxazolidinedione This compound was prepared according to the procedure described in Example 2, STEP B.

$^1$H NMR (400 MHz, CDCl$_3$): δ 8.03 (brs, 1H), 7.4–6.8 (m, 7H); 5.76 (s, 1H); 4.2 (t, 2H, J=6.0 Hz), 4.15 (t, 2H, J=5.8 Hz); 2.57 (t, 2H, 7.4 Hz); 2.4–1.8 (m, 13H); 0.94 (t, 3H, J=7.2 Hz).

Example 7

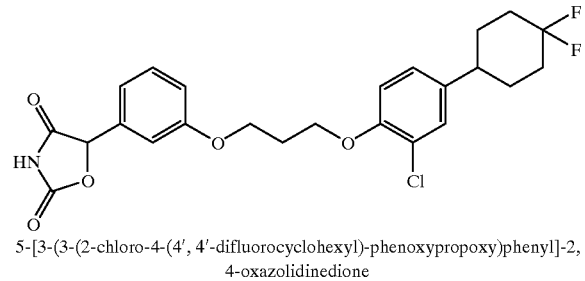

5-[3-(3-(2-chloro-4-(4',4'-difluorocyclohexyl)-phenoxypropoxy)phenyl]-2,4-oxazolidinedione Step A: Preparation of 2-chloro-4-(4',4,-difluorocyclohexyl)phenol Commercially available 4-(4-hydroxyphenyl)cyclohexanone was first converted to the corresponding gem difluoro analog using bis(2-methoxyethyl)amino sulfur trifluoride according to procedure described in the Example 6, Step A. To a solution of this 4-(4-hydroxyphenyl)-1,1'-difluorocyclohexane (1.1 g) in toluene (15 mL) was added diisobutylamine(0.062 mL) and sulfuryl chloride (0.29 mL), and the mixture was stirred at 70° C. for 3–4 h. Excess reagents were removed under the reduced pressure. The residue was diluted with ethyl acetate and the organic phase was washed with water, saturated solution of NaHCO$_3$, then brine, and was then dried over sodium sulfate and concentrated in vacuo to afford a crude oil. The oil was subjected to silica gel chromatography using hexane-dichloromethane to furnish the title compound.

Step B: Preparation of ethyl 3-(3-(2-chloro-4-(4',4'-difluorocyclohexyl)-phenoxypropoxy)mandelate This compound was prepared according to procedure described in the Example 1, Step B–C. Step C: 5-[3-(3-(2-chloro-4-(4',4'-difluorocyclohexyl)-phenoxypropoxy)phenyl]-2,4-oxazolidinedione This compound was prepared according to the procedure described in the Example 2, Step B.

$^1$H NMR (400 MHz, CDCl$_3$): δ 8.05 (brs, 1H), 7.4–6.8 (m, 7H); 5.77 (s, 1H); 4.25–4.2 (m, 4H); 4.15 (t, 2H, J=5.8 Hz); 2.6–1.6 (m, 11H).

Example 8

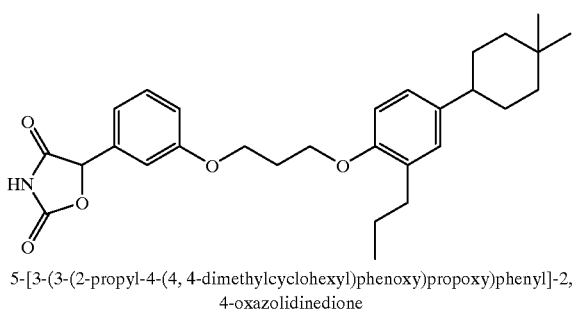

5-[3-(3-(2-propyl-4-(4, 4-dimethylcyclohexyl)phenoxy)propoxy)phenyl]-2, 4-oxazolidinedione Step A: Preparation of 4,4-dimethylcyclohexyl-1-one A solution of 4,4-dimethyl-2-cyclohexene-1-one (5.6 g, 0.94 mmol) in ethanol (45 mL) was degassed and purged with nitrogen, 10% palladium on carbon was added, the reaction was degassed and purged with hydrogen. The mixture was stirred at room temperature overnight under an atmosphere of hydrogen and filtered through celite. The filtrate was evaporated to afford the title compound (5.0 g).

$^1$HNMR (400 MHz, CDCl$_3$): δ 2.33–2.37 (t, 4H, J=7.05 Hz), 1.64–1.69 (t, 4H, J=6.95 Hz), 1.1 (s, 6H).

Step B: Preparation of 4-(1-hydroxyl-4,4-dimethylcyclohexyl)allyloxyphenol

A solution of dried magnesium (0.583 g, 24.0 mmol), 1,2-dibromobenzene (3 drops), 4-bromo allyloxyphenol (4.1 g, 19.2 mmol), in ethyl ether (20 mL) was stirred at reflux for 1–2 h. The solution was cooled and added to a solution of 4,4-dimethylcyclohexyl-1-one (2.0 g, 16.0 mmol) in ethyl ether (10 mL) and stirred at reflux for 1–2 h. The reaction mixture was cooled and treated with 2N hydrochloric acid, diluted with ethyl acetate, and washed with water and brine. The organic layer was dried over sodium sulfate, filtered and evaporated to an oil. The resulting oil was chromatographed on silica gel, using 100% toluene, to afford the title compound (1.69 g).

$^1$HNMR (400 MHz, CDCl$_3$): δ 7.46–7.43 (d, 2H); 6.93–9.90 (d, 2H); 6.11–6.04 (m, 1H); 5.46–5.27 (dd, 2H); 4.56–4.54 (d, 2H); 2.33–1.21 (m, 8H), 1.1 (s, 6H).

Step C: Preparation of 4-(4,4-dimethyl-1-cyclohexene) allyloxyphenol

A solution of 4-(1-hydroxyl-4,4-dimethylcyclohexyl) allyloxyphenol (1.69 g), concentrated HCl (1 mL) in ethanol (10 mL) was stirred at 50° C. for 1–2 h. The mixture was cooled and partitioned between ethyl acetate and aqueous sodium bicarbonate. The organic layer was washed with water, brine, and dried over sodium sulfate. The organic layer was then filtered and the solvent removed in vacuo. The resulting oil was chromatographed on silica gel, using toluene/hexane (1:1), to afford the title compound (0.611 g).

$^1$HNMR (400 MHz, CDCl$_3$): δ 7.35–7.33 (d, 2H); 6.89–6.86 (d, 2H); 6.11–6.00 (m, 2H); 5.99–5.28 (dd, 2H); 4.56–4.53 (d, 2H); 2.42–2.40 (m, 2H); 2.01–1.99 (m, 2H); 1.56–1.51 (t, 2H, J=6.5 Hz); 0.970 (s, 6H).

Step D: Preparation of 2-allyl-4-(4,4-dimethyl-1-cyclohexene) phenol

A solution of 4-(4,4-dimethyl-1-cyclohexene) allyloxyphenol (0.611 g) in trichlorobenzene was stirred at reflux overnight. The mixture was cooled to room temperature and chromatographed over silica gel, using methylene chloride/hexane (1:1), to afford the title compound (0.389 g)

$^1$HNMR (400 MHz, CDCl$_3$): δ 7.24–7.17 (m, 2H); 6.78–6.76 (d, 1H); 6.05–5.97 (m, 2H); 5.21–5.16 (m, 2H); 4.89 (s, 1H); 3.43–3.42 (d, 2H); 2.42–2.37 (m, 2H); 2.01–1.97 (m, 2H); 1.54–1.51 (m, 2H); 0.97 (s, 6H).

Step E: Preparation of 2-propyl-4-(4.4-dimethylcyclohexyl) phenol

A solution of 2-allyl-4-(4,4-dimethyl-1-cyclohexene) phenol (0.389 g) in ethyl acetate (10 mL) was degassed and purged with nitrogen, 10% palladium on carbon was added, the reaction was degassed and purged with hydrogen. The mixture was stirred at room temperature overnight under an atmosphere of hydrogen and filtered through celite. The filtrate was evaporated to afford the title compound (0.369 g).

$^1$HNMR (400 MHz, CDCl$_3$): δ 6.98–6.94 (m, 2H); 6.72–6.70 (d, 1H); 4.50 (s, 1H); 2.60–2.56 (t, 2H, J=7.7 Hz); 2.34 (m, 1H); 1.69–1.27 (m, 10H); 0.983 (s, 6H).

Step F: 5-[3-(3-(2-propyl4-(4,4-dimethylcyclohexyl) phenoxy)propoxy)phenyl]-2,4-oxazolidinedione The title compound was prepared according to the method described in Example 2 steps A and B, using 2-propyl-4-(4,4-dimethylcyclohexyl)phenol as the starting material in step A.

$^1$HNMR (400 MHz, CDCl$_3$): δ 7.79 (bs, 1H); 7.38–7.34 (m, 1H); 7.24–7.00 (m, 5H); 6.99–6.78 (d, 1H); 5.75 (s, 1H); 4.22–4.19 (t, 2H, J=6.1 Hz); 4.15–4.12 (t, 2H, J=6.0 Hz); 2.59–2.55 (t, 2H, J=7.5 Hz); 2.30–2.20 (m, 3H); 1.69–1.29 (m, 10H); 0.983–0.857(s, 9H). MS: m/e=502 (m+Na).

Example 9

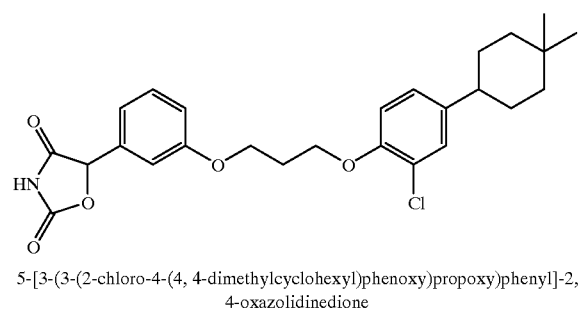

5-[3-(3-(2-chloro-4-(4, 4-dimethylcyclohexyl)phenoxy)propoxy)phenyl]-2, 4-oxazolidinedione Step A: Preparation of 4-(1-hydroxyl4,4-dimethyicyclohexyl)anisole A solution of 4-methoxyphenylmagnesium bromide (56 mL, 27.8 mmol), 4,4-dimethylcyclohexyl-1-one (3.2 g, 25.4 mmol), in THF (30 mL) was stirred at room temperature overnight. The reaction mixture was treated with 2N hydrochloric acid and diluted with ethyl acetate. The organic layer was washed with water and brine, dried over sodium sulfate, filtered and evaporated to an oil. The resulting oil was chromatographed on silica gel, using a gradient of toluene/ethyl acetate (18:1), to afford the title compound (1.77 g).

$^1$H NMR (400 Hz, CDCl$_3$): δ 7.45 (d, 2H); 6.91 (d, 2H); 3.82 (s, 3H); 2.01–1.96 (m, 2H); 1.72–1.66 (m, 3H); 1.54–1.51 (m, 2H); 1.33–1.31 (m, 2H); 1.1–1.01 (d, 6H).

Step B: Preparation of 4-(4,4-dimethyl-1-cyclohexene) anisole

Using 4-(1-hyroxyl-4,4-dimethylcyclohexyl)anisole, this compound was prepared in a similar manner as described for the preparation of EXAMPLE 8 (STEP C) (5.9 g).

$^1$H NMR (400 MHz, CDCl$_3$): δ 7.35–7.34 (d, 2H); 6.87–6.85 (d, 2H); 5.99–5.97 (bs, 1H); 3.82 (s, 3H); 2.42–2.40 (m, 2H); 2.0–1.98 (m, 2H); 1.54–1.51 (t, 2H); 0.968 (s, 6H);

Step C: Preparation of 4-(4,4-dimethylcyclohexyl)anisole

Using 4-(4,4-dimethyl-1-cyclohexene)anisole, this compound was prepared in a similar ma nner as described for the preparation of EXAMPLE 8 (STEP A) (5.7 g ).

$^1$H NMR (400 MHz, CDCl$_3$): δ 7.17–7.15 (d, 2H); 6.86–6.84 (d, 2H); 3.81 (s, 3H); 2.41–2.35 (m, 1H); 1.70–1.30 (m, 8H); 0.968 (d, 6H);

Step D: Preparation of 4-(4,4-dimethylcyclohexyl)phenol

A solution of 4-(4,4-dimethylcyclohexyl)anisole (2.76 g, 12.64 mmol), boron tribromide (4.42 mL, 15.2 mmol), in methylene chloride was stirred at room temperature overnight. The reaction mixture was treated with wet ice and diluted with methylene chloride. The organic layer was washed with water and brine. The organic layer was dried over sodium sulfate, filtered, and concentrated in vacuo. The product was chromatographed on silica gel, using a toluene/ethyl acetate (18:1), to afford the title compound (2.19 g).

$^1$H NMR (400 MHz, CDCl$_3$): δ 7.27–7.10 (d, 2H); 6.78–6.76 (d, 2H); 2.37–2.33 (m, 1H); 1.69–1.29 (m, 8H); 0.78–0.961 (d, 6H);

Step E: Preparation of 2-chloro-4-(4,4-dimethylcyclohexyl) phenol

A solution of 4-(4,4-dimethylcyclohexyl)phenol (2.16 g, 10.6 mmol), disiobutylamine (0.14 mL) and sulfuryl chloride (0.59 mL, 7.4 mmol) in toluene was stirred at 70° C. for 2 h. The reaction mixture was cooled to room temperature, treated with saturated aqueous sodium bicarbonate and diluted with ethyl acetate. The organic layer was washed with water, brine, dried over sodium sulfate, filtered and concentrated in vaclio. The resulting oil was subjected to chromatography on silica gel, using hexane/ethyl acetate (20:1), to afford the title compound (1.7 g).

$^1$H NMR (400 MHz, CDCl$_3$): δ 7.18 (s, 1H); 7.05–7.03 (d, 1H); 6.95–6.93 (d, 1H); 5.36 (s, 1H); 2.37–2.30 (m, 1H); 1.69–1.29 (m, 8H); 0.976–0.850 (d, 6H);

Step F: 5-[3-(3-(2-chloro-4-(4.4-dimethylcyclohexyl) phenoxy)propoxy)phenyl]-2,4-oxazolidinedione The title compound was prepared according to the method described in Example 2 steps A and B, using 2-chloro-4-(4,4-dimethylcyclohexyl)phenol, as the starting material in step A.

$^1$H NMR (400 MHz, CDCl$_3$): δ 7.80 (brs, 1H); 7.38–6.87 (m,7H); 5.74 (s, 1H); 4.25–4.19 (m, 4H); 2.35–2.29 (m, 3H); 1.68–1.27 (m, 8H); 0.973–0.958 (d, 6H). MS: m/e=494 (M+Na).

Example 10

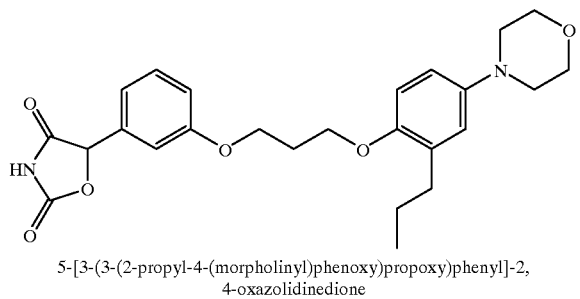

5-[3-(3-(2-propyl-4-(morpholinyl)phenoxy)propoxy)phenyl]-2,4-oxazolidinedione

Step A: Preparation of 2-propyl-4-morpholinyl-1-benzyloxybenzene

A solution of 3-propyl-4-benzyloxy-1-bromobenzene (1.0 g, 3.3 mmol), morpholine (0.5 g, 6.6 mmol), Pd(OAc)$_2$ (0.036 g, 0.16 mmol), BINAP (0.082 g, 0.132 mmol) and cesium carbonate (1.50 g, 4.62 mmol) in toluene (134 mL) was degassed and purged with nitrogen. The reaction mixture was stirred at 100° C. overnight. The reaction mixture was cooled to room temperature and partitioned between ethyl acetate and 10% aqueous citric acid. The organic layer was washed with water and brine. The organic layer was dried over sodium sulfate, filtered and evaporated to an oil. The resulting oil was chromatographed on silica gel, using toluene with 5% ethyl acetate, to afford the title compound (1.03 g).

$^1$H NMR (400 MHz, CDCl$_3$): δ 7.45–6.70 (m, 8H); 5.04 (s, 2H); 3.88–3.86 (m, 4H); 3.09–3.06 (m, 4H); 2.66–2.62 (t, 2H) 1.68–1.65 (q, 2H); 0.990–0.953 (t, 3H).

Step B: Preparation of 2-propyl-4-morpholinyl phenol

A solution of 2-propyl-4-morpholinyl-1-benzyloxybenzene (0.0811 g) in ethyl acetate (10 mL)/acetic acid (2 mL) was degassed and purged with nitrogen, 10% palladium on carbon was added, the reaction mixture was degassed and purged with hydrogen. The mixture was stirred at room temperature overnight under an atmosphere of hydrogen and filtered through celite. The filtrate was evaporated to afford the title compound (0.430 g).

$^1$H NMR (400 MHz, CDCl$_3$): δ 6.75–6.67 (m, 3H); 4.45 (s, 1H); 3.88–3.86 (m, 4H); 3.07–3.05 (m, 4H); 2.59–2.55 (t, 2H) 1.68–1.62 (q, 2H); 1.01–0.975 (t, 3H).

Step C: 5-[3-(3-(2-propyl-4-(morpholinyl)phenoxy) propoxy)phenyl]-2 4-oxazolidinedione The title compound was prepared according to the method described in Example 2 steps A and B, using 2-propyl-4-morpholinyl phenol as the starting material in step A.

$^1$H NMR (400 MHz, CDCl$_3$): δ 7.37–7.35 (t, 1H); 7.02–6.72 (m, 7H); 5.74 (s, 1H); 4.20–4.11 (dt, 4H); 3.89–3.87 (m, 4H); 3.09–3.07 (m, 4H); 2.57–2.53 (t, 2H); 2.28–2.25 (t, 2H, J=6.1 Hz); 1.60–1.55 (q, 2H, J=7.4 Hz); 0.939–0.903 (J=7.2 Hz). MS: m/e=455.4 (M+).

Example 11

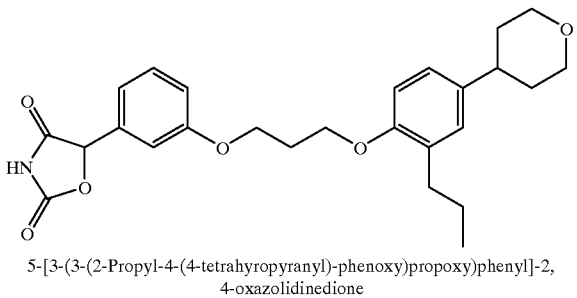

5-[3-(3-(2-Propyl-4-(4-tetrahyropyranyl)-phenoxy)propoxy)phenyl]-2,4-oxazolidinedione Step A: 4-Bromo-2-propylphenol The title compound was prepared from 4-bromophenol following the procedure described in Example 1 Step A, except that the hydrogenation was conducted using platinum oxide as catalyst, ethyl acetate as solvent, under 30 psi hydrogen pressure.

4-bromo-2-propylphenol:
$^1$H NMR (500 MHz, CDCl$_3$): δ δ 7.25 (d, J=2.5 Hz, 1H), 7.19 (dd, J=2.5 Hz, 8.5 Hz, 1H), 6.66 (d, J=8.5 Hz, 1H), 4.72 (brs, 1H), 2.56 (t, J=7.3 Hz, 2H), 1.65 (seq., J=7.6 Hz, 2H), 0.99 (t, J=7.3 Hz, 3H).

Step B: Benzyl 2-Propyl-4-(4-(4-hyroxyl-tetrahydropyranyl))phenyl ether

To a 100 ml acetone solution of 4-bromo-2-propylphenol 5.4 g (25.1 mmol) and benzyl bromide 5.6 g (32.7 mmol) was added potassium carbonate 5.2 g (37.6 mmo). Resulting suspension was stirred under reflux temperature for overnight. Acetone was removed under reduced pressure, diluted with ethyl acetate and water. Organic phase was separated. Aqueous phase was extracted with ethyl acetate twice. The combined organic phases were dried over anhydrous sodium sulfate, filtered, concentrated, chromatographed on silica gel (hexanes:t-butyl methyl ether) to give 6.96 g of benzyl 4-bromo-2-propylphenyl ether as colorless oil.

To a 2 ml dry THF suspension of magnesium turnings 750 mg (30.9 mmol) was slowly added benzyl 4-bromo-2-propylphenyl ether 3.5 g (11.5 mmol) over 30 min with occasional heating by a heat gun and addition of 13 ml of dry THF. After the addition was complete, resulting dark gray suspension was heated to 40–50° C. for 1 hr. To resulting suspension of 4-benzyloxy-2-propylphenyl magnesium bromide was added 15 ml of dry THF solution of tetrahydro-4H-pyran-4-one 861 mg (8.63 mmol) while cooled in a ice-water bath. After stirring overnight at rt, THF was removed under reduced pressure, diluted with ethyl acetate and saturated aqueous ammonium chloride solution. Organic phase was separated. Aqueous phase was extracted twice with ethyl acetate. The combined organic phases were dried over anhydrous sodium sulfate, filtered, concentrated, chromatographed on silica gel (hexanes:ethyl acetate) to give 1.88 g of the title compound as white solid.

Benzyl 2-Propyl-4-(4-(4-hyroxyl-tetrahydropyrayl)) phenyl ether:
$^1$H NMR (500 MHz, CDCl$_3$): δ 7.46–7.32 (m, 5H), 7.31 (d, J=2.4 Hz, 1H), 7.27 (dd, J=2.4 Hz, 8.5 Hz, 1H), 6.90 (d, J=8.5 Hz, 1H), 5.12 (s, 2H), 4.0–3.8 (m, 4H), 2.69 (t, J=7.7 Hz, 2H), 2.21–2.15 (m, 2H), 1.76–1.62 (m, 4H), 0.98 (t, J=7.4 Hz, 3H).

Step C: 2-Propyl-4-(4-tetrahvdropyranyl)phenol

To a 30 ml 1,2-dichloroethane solution of benzyl 2-propyl-4-(4-(4-hyroxyl-tetrahydropyranyl))phenyl ether 1.85 g (567 mmol) were added diisopropyl ethyl amine 2.4 ml (13.8 mmol), and methanesulfonic anhydride 1.28 g (7.34 mmol). After stirring at rt overnight, the solvent was removed under reduced pressure, diluted with ethyl acetate and water. Organic phase was separated. Aqueous phase was extracted twice with ethyl acetate. The combined organic phases were dried over anhydrous sodium sulfate, filtered, concentrated, chromatographed on silica gel (hexanes:t-butyl methyl ether) to give 0.875 g of benzyl 2-propyl-4-(4-(5,6-dihyro-2H-pryanyl))phenyl ether.

Benzyl 2-propyl-4-(4-(5,6-dihyro-2H-pryanyl))phenyl ether:
$^1$H NMR (500 MHz, CDCl$_3$): δ 7.48–7.32 (m, 5H), 7.24 (d, J=2.4 Hz, 1H), 7.19 (dd, J=2.4 Hz, 8.5 Hz, 1H), 6.88 (d, J=8.5 Hz, 1H), 6.04 (brs, 1H), 5.11 (s, 2H), 4.33 (app. q., J=2.7Hz, 2H), 3.95 (app. t., 2H), 2.69 (t, J=7.5Hz, 2H), 2.52 (brs, 2H), 1.68 (seq., J=7.5 Hz, 2H), 0.99 (t., J=7.4 Hz, 3H).

To a 30 ml 190-proof ethanol solution of benzyl 2-propyl-4-(4-(5,6-dihyro-2H-pryanyl))phenyl ether 0.875 g (2.84 mmol) was added 10% Pd/C 45 mg. This suspension was placed in a Parr shaker under a hydrogen atmosphere (50 psi) overnight. The reaction mixture was filtered through celite, concentrated, chromatographed on Silica gel (hexanes: ethyl acetate) to give 0.573 g of the title compound.

2-Propyl-4-(4-tetrahydropyrayl)-phenol:
$^1$H NMR (500 MHz, CDCl$_3$): δ 6.98 (d, J=2.3 Hz, 1H), 6.94 (dd, J=2.3 Hz, 8 Hz, 1H), 6.73 (d, J=8 Hz, 1H), 4.08 (m, 2H), 3.52 (t, J=7.4 Hz, 2H), 2.7–2.55 (m, 4H), 1.75 (m, 3H), 1.66 (seq., J=7.4 Hz, 2H), 1.00 (t, J=7.4 Hz, 3H).

Step D: 5-[3-(3-(2-Propyl-4-(4-tetrahyropyranyl)-phenoxy)propoxy)phenyl]-2.4-oxazolidinedione 2-Propyl-4-(4-tetrahydropyrayl)phenol was treated as described in Example 1 Step C–E, to give the title compound.

5-[3-(3-(2-Propyl-4-(4-tetrahyropyranyl)phenoxy)propoxy)phenyl]-2,4-oxazolidinedione;
$^1$H NMR (500 MHz, CDCl$_3$): δ 8.08 (brs, 1H), 7.36 (app.t., J=8 Hz, 1H), 7.04–6.86 (m, 4H), 6.82 (d, J=8 Hz, 1H), 5.77 (s, 1H), 4.21 (t, J=6.2 Hz, 2H), 4.15 (t, J=6.2Hz, 2H), 4.08 (dd, J=3.5Hz, 11.1 Hz, 2H), 3.53 (dt, J=2.5 Hz, 9 Hz), 2.69 (m, 1H), 2.58 (t, J=7.6 Hz, 2H), 1.8–1.7 (m, 4H), 1.65–1.55 (m, 4H), 0.94 (t, J=7.3 Hz, 3H). MS m/e=454 (M$^+$+H).

Example 12

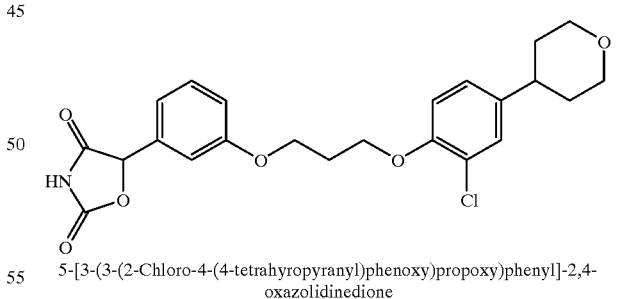

5-[3-(3-(2-Chloro-4-(4-tetrahyropyranyl)phenoxy)propoxy)phenyl]-2,4-oxazolidinedione Step A: 4-(4-Tetrahydropyranyl)-phenol 4-Bromo phenol was treated as described in EXAPLE 11 Step B–C to give the title compound.

4-(4-Tetrahydropyranyl)phenol:
$^1$H NMR (500 MHz, CDCl$_3$): δ 7.11 (d, J=8.5 Hz, 2H), 6.81 (d, J=8.5Hz, 2H), 5.03 (brs, 1H), 4.10 (app.d, 2H), 3.55 (app.dt, 2H), 2.71 (tt, 1H), 1.85–1.75 (m, 4H).

Step B: 2-Chloro-4-(4-tetrahydropyranyl)phenol

To a 30ml Toluene solution of 4-(4-tetrahydropyranyl) phenol 1 g (5.61 mmol) and diisobutylamine 0.08 ml (0.46 mmol) was added sulfuryl chloride 0.51 ml (6.35 mmol) over 3 hr period upon heating at 70° C. Stirring was continued at that temp. for 2 hr after the addition of sulfuryl chloride was complete. The solvent was removed under reduced pressure, diluted with ethyl acetate and washed with 2N aqueous HCl, saturated aqueous sodium bicarbonate solution, dried over anhydrous sodium sulfate, filtered, concentrated, chromatographed on silica gel (hexanes:ethyl acetate) to give 0.941 g of the title compound as while solid.
2-Chloro-4-(4-tetrahydropyranyl)phenol:
$^1$H NMR (500MHz, CDCl$_3$): δ 7.19 (s, 1H), 7.06 (d, J=8.5 Hz, 1H), 6.99 (d, J=8.5 Hz, 1H), 5.44 (brs, 1H), 4.09 (app.d, 2H), 3.53 (m, 2H), 2.70 (tt, 1H), 1.80 (m, 4H).
Step C: 5-[3-(3-(2-Chloro-4-(4-tetrahyropyranyl)-phenoxy)propoxy)phenyl]-2,4-oxazolidinedione
2-Chloro-4-(4-tetrahydropyranyl)phenol was treated as described in Example 2 Step A–B to give the title compound.
5-[3-(3-(2-Chloro-4-(4-tetrahyropyranyl)phenoxy)propoxy)phenyl] -2,4-oxazolidinedione:
$^1$H NMR (500 MHz, CDCl$_3$): δ 8.67 (brs, 1H), 7.34 (t, J=8.4 Hz, 1H), 7.24 (d, J=2.1 Hz, 1H),7.08 (dd, J=2.1 Hz, 8.4 Hz, 1H), 7.04 (d, J=7.8 Hz, 1H), 7.00 (s, 1H), 6.93 (d, J=8.4 Hz, 1H), 5.78 (s, 1H), 4.26 (m, 4H), 4.11 (d, J=11 Hz, 2H), 3.54 (m, 2H), 2.71 (tt, 1H), 2.33 (app. seq. 2H), 1.77 (m, 4H). MS m/e=446(M$^+$+H).

What is claimed is:

1. A compound having the formula I:

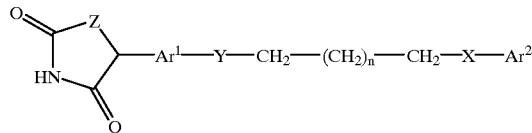

I wherein
Ar$^1$ is
(1) arylene or
(2) heteroarylene,
wherein said arylene or heteroarylene is optionally substituted with from 1 to 4 groups independently selected from R$^a$, R, or a mixture thereof,
Ar$^2$ is
(1) aryl or
(2) heteroaryl,
wherein said aryl or heteroaryl is substituted with 1–2 groups independently selected from R, provided that if only one cycloalkyl is present on Ar$^2$, the cycloalkyl is not in the ortho position, and said aryl or heteroaryl is optionally further substituted with from 1–3 groups independently selected from R$^a$;
X and Y are independently O, S, N—R$^b$, or CH$_2$;
Z is O;
n is 0 to 3;
R is
(1) C$_{3-8}$ cycloalkyl, optionally substituted with 1–15 halogen atoms, 1–3 groups independently selected from C$_{1-6}$ alkyl, and mixtures thereof; or
(2) a 3–10 membered heterocycle containing one or more heteroatoms selected from N, S, O, and SO$_2$, said heterocycle being optionally substituted with 1–3 halogen atoms or one to three C$_{1-6}$ alkyl groups;
R$^a$ is
(1) C$_{1-15}$ alkanoyl,
(2) C$_{1-15}$ alkyl,
(3) C$_{2-15}$ alkenyl,
(4) C$_{2-15}$ alkynyl,
(5) halo,
(6) OR$^b$,
(7) aryl, or
(8) heteroaryl,
wherein said alkyl, alkenyl, alkynyl, and alkanoyl are optionally substituted with from 1–5 groups selected from R$^c$, and said aryl and heteroaryl are optionally substituted with 1 to 5 groups selected from R$^d$;
R$^b$ is
(1) hydrogen,
(2) C$_{1-10}$alkyl,
(3) C$_{2-10}$alkenyl,
(4) C$_{2-10}$alkynyl,
(5) aryl,
(6) heteroaryl,
(7) aryl C$_{1-15}$ alkyl,
(8) heteroaryl C$_{1-15}$ alkyl,
(9) C$_{1-15}$ alkanoyl,
(10) C$_{3-8}$ cycloalkyl,
wherein said alkyl, alkenyl, and alkynyl are optionally substituted with one to four substituents independently selected from R$^c$, and said cycloalkyl, aryl and heteroaryl are optionally substituted with one to four substituents independently selected from R$^d$;
R$^c$ is
(1) halo,
(2) aryl,
(3) heteroaryl,
(4) CN,
(5) NO$_2$,
(6) OR$^f$;
(7) S(O)$_m$R$^f$, m=0, 1 or 2, provided that R$^f$ is not H when m is 1 or 2;
(8) NR$^f$R$^f$,
(9) NR$^f$COR$^f$,
(10) NR$^f$CO$_2$R$^f$,
(11) NR$^f$CON(R$^f$)$_2$,
(12) NR$^f$SO$_2$R$^f$, provided that R$^f$ is not H,
(13) COR$^f$,
(14) CO$_2$R$^f$,
(15) CON(R$^f$)$_2$,
(16) SO$_2$N(R$^f$)$_2$,
(17) OCON(R$^f$)$_2$, or
(18) C$_{3-8}$cycloalkyl,
wherein said cycloalkyl, aryl and heteroaryl are optionally substituted with 1 to 3 groups independently selected from halo and C$_{1-6}$ alkyl;
R$^d$ is
(1) a group selected from R$^c$,
(2) C$_{1-10}$ alkyl,
(3) C$_{2-10}$ alkenyl,
(4) C$_{2-10}$ alkynyl,
(5) aryl C$_{1-10}$ alkyl, or
(6) heteroaryl C$_{1-10}$ alkyl,
wherein said alkyl, alkenyl, alkynyl, aryl C$_{1-10}$ alkyl, and heteroaryl C$_{1-10}$ alkyl are optionally substituted with a group independently selected from R$^e$;
R$^e$ is
(1) halogen,
(2) amino,
(3) carboxy,
(4) C$_{1-4}$alkyl,
(5) C$_{1-4}$alkoxy, (6) hydroxy,
(7) aryl,
(8) aryl $C_{1-4}$ alkyl, or
(9) aryloxy;

$R^f$ is
(1) hydrogen,
(2) $C_{1-10}$ alkyl,
(3) $C_{2-10}$ alkenyl,
(4) $C_{2-10}$ alkynyl,
(5) aryl,
(6) heteroaryl,
(7) aryl $C_{1-15}$ alkyl,
(8) heteroaryl $C_{1-15}$ alkyl,
(9) $C_{1-15}$ alkanoyl,
(10) $C_{3-8}$ cycloalkyl;
  wherein said alkyl, alkenyl, alkynyl, aryl, heteroaryl, alkanoyl and cycloalkyl are optionally substituted with one to four groups independently selected from $R^e$;

or a pharmaceutically acceptable salt thereof.

2. A compound of claim 1 wherein $Ar^1$ is arylene optionally substituted with 1–4 groups independently selected from $R^a$, R, or a mixture thereof.

3. A compound of claim 1 wherein $Ar^1$ is phenylene optionally substituted with 1–2 groups independently selected from halogen and $C_{1-4}$ alkyl.

4. A compound of claim 1 wherein X and Y are independently $CH_2$, O or S.

5. A compound of claim 3 wherein X and Y are each O or S.

6. A compound of claim 1, wherein $Ar^2$ is aryl, wherein said aryl is substituted with one $R^a$ group in the position ortho to X and is further substituted with 1–2 groups independently selected from R and optionally 1–2 groups independently selected from Ra.

7. A compound of claim 6 wherein said $R^a$ that is in the position ortho to X is selected from the group consisting of:

(1) $C_{3-10}$ alkyl optionally substituted with 1–4 groups independently selected from halo and $C_{3-6}$cycloalkyl,
(2) $C_{3-10}$ alkenyl, and
(3) $C_{3-8}$ cycloalkyl.

8. A compound of claim 7 wherein $Ar^2$ is a phenyl ring.

9. A compound according to claim 8, wherein two of the optional substituents $R^a$ are on adjacent carbon atoms in said $Ar^2$ phenyl ring and are joined to form a 5- or 6-membered aromatic heterocyclic ring fused to $Ar^2$, said ring containing 1–2 heteroatoms independently selected from N, O, and S(O)m, where m is 0–2, said heterocyclic ring and $Ar^2$ together being substituted with 1–2 groups independently selected from R, one $R^a$ group in the position ortho to X, and optionally 1–2 additional groups independently selected from $R^a$.

10. A compound according to claim 9, wherein said aromatic heterocyclic ring fused to $Ar^2$ is selected from isoxazole, thiophene, thiophene S-oxide, thiophene S-dioxide, and furan.

11. A compound of claim 1 wherein n is 1 or 2.

12. A compound of claim 1 having the formula Ia:

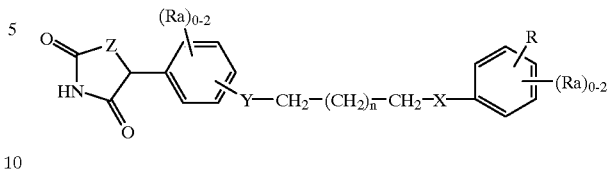

Ia wherein X, Y, Z, n, R, and $R^a$ are as in claim 1.

13. A compound of claim 12 wherein Y is S or O, and X is O.

14. A compound of claim 12 wherein one Ra group is ortho to X and is $C_{3-4}$ alkyl.

15. A compound of claim 12 wherein n is 1 or 2.

16. A compound of claim 12 wherein
X is O;
Y is
  (1) O or
  (2) S; and
one group Ra is ortho to X and is $C_{3-4}$ alkyl.

17. A compound of claim 16 wherein R is cyclohexyl.

18. A compound of claim 1 selected from the group consisting of:

5-[3-(3-(2-propyl-4-cyclohexylphenoxy)propoxy)phenyl]-2,4-oxazolidinedione;

5-[3-(3-(2-propyl-4-cyclopentylphenoxy)propoxy)phenyl]-2,4-oxazolidinedione;

5-[3-(3-(2-chloro-4-cyclopentylphenoxy)propoxy)phenyl]-2,4-oxazolidinedione;

5-[3-(3-(2-propyl-4-(4',4'-difluorocyclohexyl)-phenoxypropoxy)phenyl]-2,4-oxazolidinedione;

5-[3-(3-(2-chloro-4-(4',4'-difluorocyclohexyl)-phenoxypropoxy)phenyl]-2,4-oxazolidinedion 5-[3-(3-(2-propyl-4-(4,4-dimethylcyclohexyl)phenoxy)propoxy)phenyl]-2,4-oxazolidinedione;

5-[3-(3-(2-chloro-4-(4,4-dimethylcyclohexyl)phenoxy)propoxy)phenyl]-2,4-oxazolidinedione;

5-[3-(3-(2-propyl-4-(morpholinyl)phenoxy)propoxy)phenyl]-2,4-oxazolidinedione;

5-[3-(3-(2-Propyl-4-(4-tetrahyropyranyl)-phenoxy)propoxy)phenyl]-2,4-oxazolidinedione; and 5-[3-(3-(2-Chloro-4-(4-tetrahyropyranyl)phenoxy)propoxy)phenyl]-2,4-oxazolidinedione.

19. A pharmaceutical composition comprising a compound of claim 1 and a pharmaceutically acceptable carrier.

20. A method for treating or controlling diabetes mellitus in a mammal which comprises administering to said mammal a therapeutically effective amount of a compound of claim 1.

21. A method for treating or controlling hyperglycemia in a mammal which comprises administering to said mammal a therapeutically effective amount of a compound of claim 1.

22. A method for treating or controlling hyperlipidemia in a mammal which comprises administering to said mammal a therapeutically effective amount of a compound of claim 1.

23. A method for treating or controlling obesity in a mammal which comprises administering to said mammal a therapeutically effective amount of a compound of claim 1.

24. A method for treating or controlling hypercholesterolemia in a mammal which comprises administering to said mammal a therapeutically effective amount of a compound of claim 1.

25. A method for treating or controlling hypertriglyceridemia in a mammal which comprises administering to said mammal a therapeutically effective amount of a compound of claim 1.

26. A method for treating or controlling dyslipidemia in a mammal which comprises administering to said mammal a therapeutically effective amount of a compound of claim 1.

27. A compound according to claim 1 having a structure selected from the group consisting of:

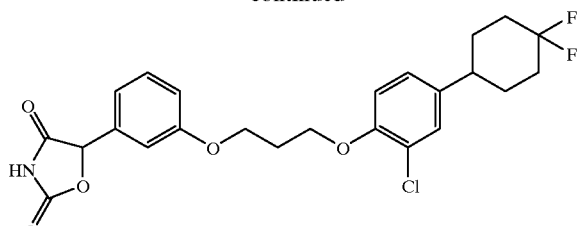

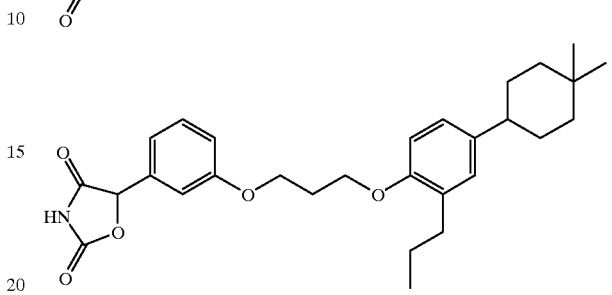

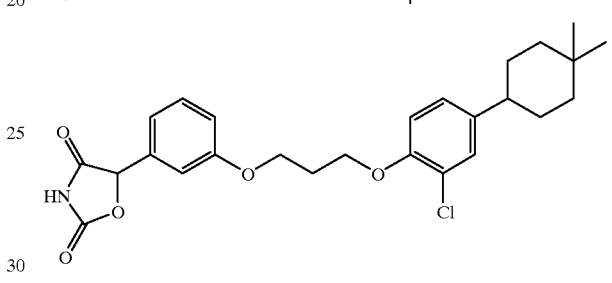

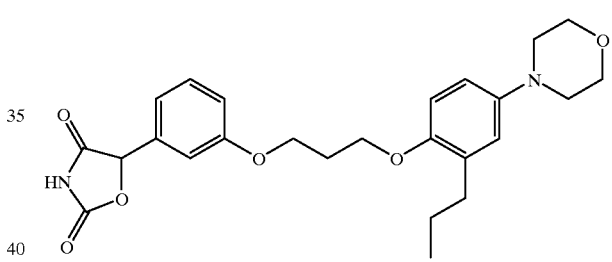

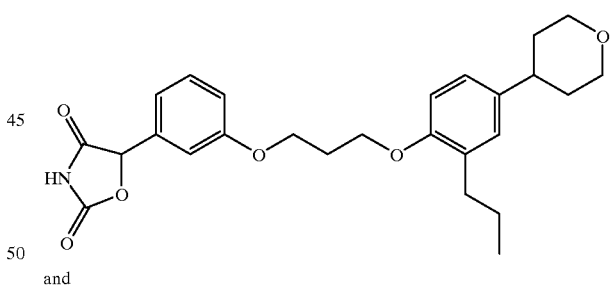

and

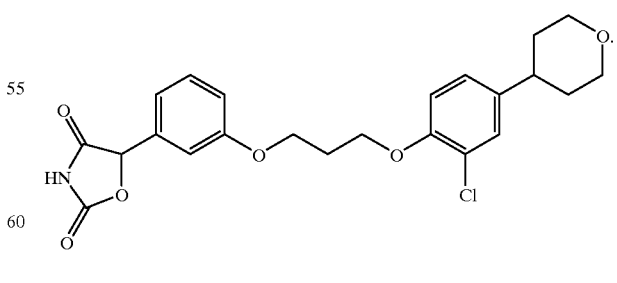

* * * * *